(12) United States Patent
Lin

(10) Patent No.: US 12,324,904 B2
(45) Date of Patent: Jun. 10, 2025

(54) ELECTRIC INJECTION DEVICE

(71) Applicant: Tsai-Ming Lin, Kaohsiung (TW)

(72) Inventor: Tsai-Ming Lin, Kaohsiung (TW)

( * ) Notice: Subject to any disclaimer, the term of this patent is extended or adjusted under 35 U.S.C. 154(b) by 975 days.

(21) Appl. No.: 17/398,119

(22) Filed: Aug. 10, 2021

(65) Prior Publication Data
US 2023/0050647 A1  Feb. 16, 2023

(51) Int. Cl.
*A61M 5/315* (2006.01)

(52) U.S. Cl.
CPC .... *A61M 5/31576* (2013.01); *A61M 5/31501* (2013.01); *A61M 5/31511* (2013.01); *A61M 2005/3152* (2013.01); *A61M 2005/31588* (2013.01); *A61M 2205/8206* (2013.01)

(58) Field of Classification Search
CPC .......... A61M 5/31576; A61M 5/31501; A61M 5/31511; A61M 5/3158; A61M 5/20; A61M 5/31575; A61M 5/31581; A61M 5/31561; A61M 5/31563; A61M 5/31558; A61M 2005/3152; A61M 2005/31588; A61M 2205/8206
See application file for complete search history.

(56) References Cited

U.S. PATENT DOCUMENTS

| | | | | | |
|---|---|---|---|---|---|
| 4,158,246 | A | * | 6/1979 | Meadows | A46B 13/02 15/28 |
| 6,309,375 | B1 | * | 10/2001 | Glines | A61B 17/3478 604/207 |
| 2004/0073168 | A1 | | 4/2004 | Takatsuka et al. | |
| 2009/0254060 | A1 | * | 10/2009 | Hetherington | A61M 5/3158 604/506 |

FOREIGN PATENT DOCUMENTS

| CN | 107261261 A | 10/2017 |
|---|---|---|
| EP | 2387962 A1 | 11/2011 |
| WO | 1999059663 A1 | 11/1999 |

* cited by examiner

*Primary Examiner* — Michael J Tsai
*Assistant Examiner* — Justin L Zamory
(74) *Attorney, Agent, or Firm* — Winston Hsu

(57) ABSTRACT

An electric injection device at least comprises an outer case, a drive mechanism, a transmission mechanism, a linkage mechanism and a push mechanism. The drive mechanism, the transmission mechanism, the linkage mechanism and the push mechanism are all assembled in the outer case, and the drive mechanism is used to drive the transmission mechanism. The transmission mechanism can transmit power to rotate a push block regularly and drive a brake end of the linkage mechanism continuously. The push mechanism comprises at least a pushing shaft and a pushing element. The brake end can continuously push the pushing element, and the pushing element propels the pushing shaft to further push a syringe assembled on the outer case, so as to use electric injection instead of manual injection to complete the syringe.

13 Claims, 14 Drawing Sheets

ELECTRIC INJECTION DEVICE

BACKGROUND OF THE INVENTION

1. Field of the Invention

The present invention relates to an electric injection device, which is an injection device enabling high-precision directional control, uniform injection and easy assembly; in particular, the disclosed injection device is driven by electric power.

2. Description of Related Art

It is well-known that autologous fat graft is often used in reconstructive surgery or aesthetic surgery, which applies the autologous fat as a kind of soft tissue fillers for filling up the hollow scars, improving wrinkles, rejuvenating facial contours, and even enhancing the appearance of the lips and the nasal root, etc. Actually, for a long time, autologous fat graft has been also regarded as a good surgical method for soft tissue transplantation or filling operations, such as large-area autologous fat transplantation, e.g., breast augmentation, buttock augmentation, or the like.

In practice, delivering the fat globules into the implanted area during the operation heavily relies on the experiences and skills of the operating surgeon. Due to such manual operations with different personal experiences, the survival rate of grafted fat is generally not good enough, adversely leading to some side effects, such as: absorption, infection, embolism, cyst formation, calcification, ossification, pseudotumor formation, necrosis, asymmetry, skin necrosis/fistula formation, iatrogenic nerve/vascular injuries and carvenous sinus thrombosis, and so forth. After some investigations, the causes of such side effects are mostly related to improper, uneven or excessive placement of fat during fat transplantation procedures.

Although there are auxiliary devices currently available on the market, the smallest precise injection volume can only be controlled down to $\frac{1}{10}$ milliliters (cc) or $\frac{1}{2}$ milliliters. The fat transplantation using these devices or tools may fail due to insufficient levels of precision and accuracy in the final implantation step, or even worse, resulting in many side effects as previously mentioned.

Therefore, how to properly, uniformly and precisely place the fat at correct positions in clinical practice has become the most important topic in fat grafting techniques. However, clinically, it is already extremely difficult to accurately push $\frac{1}{10}$ ml of fat in each injection, not to mention that if you want to precisely minimize the amount of injected fat to $\frac{1}{30}$ or $\frac{1}{50}$ ml each time, the precision as well as the accuracy requirements are indeed far beyond human control.

As a result, in accordance with the precision of the operations, the air-tightness of the equipment, the operation simplicity, and most importantly, the fineness of output (i.e., each output amount lies between $\frac{1}{30}$~$\frac{1}{240}$ cc), the electric injection device of the present invention generally applies electric power to replace existing manual operation as a driving source, thereby solving the instability caused by human operation and providing precision such that the injection operation can be effectively reduced to enable the surgeons more concentrate on injecting fat into the correct position, thereby achieving the intended operation simplicity, saving physical efforts of surgeons and increasing the number of operating tables per day, all of which constitute the solution provided by the electric injection device of the present invention.

SUMMARY OF THE INVENTION

The present invention provides an electric injection device, comprising: an outer case, installed thereon with a syringe head base; a drive mechanism, installed in the inside of the outer case and including a drive motor and a drive gear block driven by the drive motor; a transmission mechanism, installed on one side of the drive mechanism and including a gear set meshing with the drive gear block and a push block driven by the gear set; a linkage mechanism, installed on one side of the transmission mechanism and including a brake end, in which the push block pushes the linkage mechanism and makes the brake end perform reciprocating movements; and a push mechanism, installed on one side of the linkage mechanism and including a first stop block, a second stop block, a pushing shaft and a pushing element, in which the first stop block and the second stop block are installed on the inner side of the outer case, the pushing shaft is installed through the first stop block and the second stop block at the same time, a pressure board is installed at the end of the pushing shaft so that a syringe can be installed between the syringe head base and the pressure board, and in which the pushing element has a hole for the pushing element to wrap around the pushing shaft via the hole correspondingly between the brake end and the first stop block, and an abutting block is installed in the inside of the outer case so that the abutting block and the brake end are respectively located on the same side of the pushing element, wherein a first abutting elastic element wrapped around the pushing shaft is located on the other side of the pushing element, and the two ends of the first abutting elastic element respectively abut against the pushing element and one side of the first stop block thereby pushing the pushing element against the abutting block and the brake end, and the outer diameter of the hole on the pushing element is larger than that of the pushing shaft such that the pushing element will become inclined when the brake end pushes the pushing element, and, during such an inclination condition, the upper and lower edges of the hole will clamp the upper and lower surfaces of the pushing shaft to move, and then the pushing shaft can be driven to push in one direction when the pushing element is continuously pushed, so that the continuous reciprocating action of the brake end makes the pushing shaft drive the pressure board to continuously press the syringe.

In a preferred embodiment, the outer case includes a first case and a second case, and the first case is installed under the second case for hand holding, and in which the drive mechanism, the transmission mechanism and the linkage mechanism are all assembled within the first case, the push mechanism is installed within the second case, while the syringe head base is installed outside the second case.

In a preferred embodiment, the first case and the second case can be arbitrarily disassembled.

In a preferred embodiment, the two ends of the junctions between the first case and the second case are respectively installed with a pivot end and a locking end, and the pivot end is applied to pivotally connected to the second case, while the locking end is locked to the second case by means of a locking element, the pivot end can be dismantled from the second case after releasing the locking element thereby disassembling the first case and the second case.

In a preferred embodiment, the drive motor is electrically connected to a switch.

In a preferred embodiment, a touch component exposed to the outside of the outer case is installed beside the switch and is applied for hitting the switch so as to further activate the drive motor.

In a preferred embodiment, the drive motor is electrically connected to a power grid or a battery.

In a preferred embodiment, the gear set is configured with a first gear, a second gear and a third gear, and the first gear meshes with the drive gear block, the first gear and the second gear are configured to be coaxial, the second gear meshes with the third gear, the third gear and the push block are set to be coaxial, and the drive gear block drives the first gear such that the coaxial second gear rotates accordingly thereby allowing the second gear to drive the third gear to rotate the coaxial push block.

In a preferred embodiment, the number of teeth and the outer diameter of the first gear are both smaller than those of the second gear.

In a preferred embodiment, one end of the push block has a protrusion which facilitates pushing the linkage mechanism.

In a preferred embodiment, the linkage mechanism includes a first linkage rod, a reciprocating linkage rod, a reciprocating elastic element and a second linkage rod, and a first fulcrum is installed on the first linkage rod, one end of the first linkage rod is configured as a swing end, the first fulcrum is pivotally installed on the inner side of the outer case and close to the push block so that the swing end is correspondingly beside the push block, and in which the positions close to the two ends of the reciprocating linkage rod are respectively configured with a first pivot point and a second pivot point, and the other end of the first linkage rob away from the swing end is pivotally installed to the first pivot point, and the reciprocating elastic element is installed beside the first pivot point, the two ends of the reciprocating elastic element respectively abut against the inner side of the outer case and beside the first pivot point of the reciprocating linkage rod, and a second fulcrum is configured on the second linkage rod, and the brake end is installed on one end of the second linkage rod, while the other end of the second linkage rod away from the brake end is pivotally installed to the second pivot point.

In a preferred embodiment, a pulley is pivotally installed on the swing end.

In a preferred embodiment, outer side of the pushing element is further formed with a push end extending next to the brake end, in which the push end is applied to be pushed by the brake end thus further driving the pushing element.

In a preferred embodiment, the first stop block and the second stop block are installed parallel to each other on the inner side of the outer case.

In a preferred embodiment, a back stop element which includes a back stop hole is provided and wrapped around the pushing shaft via the back stop hole correspondingly between the pressure board and the second stop block, and the inside of the outer case is also installed with a back stop fulcrum and a release blockage which are respectively located on the same side of the back stop element; in addition, wherein a second abutting elastic element wrapped around the pushing shaft and a resetting block positioned under the second abutting elastic element are provided on the other side of the back stop element, in which the two ends of the second abutting elastic element respectively abut against the back stop element and one side of the second stop block thereby pushing the back stop element against the back stop fulcrum and the release blockage and allowing tilting the back stop element.

In a preferred embodiment, the release blockage includes an oblique plane, a release elastic element and a button exposed to the outside of the outer case, in which the narrower part of the oblique plane is for the back stop element to abut and push against, the two ends of the release elastic element respectively abut against the inner side of the outer case and one end of the oblique plane, and the resetting block includes a resetting elastic element and extends to a sleeve block, in which the two ends of the resetting elastic element respectively abut against the resetting block and one side of the second stop block, the sleeve block goes through the second stop block and is sleeved on the pushing shaft between the second stop block and the pushing element, such that the oblique plane can squeeze and press the release elastic element after pressing down the button, thus making the back stop element push against the wider part of the oblique plane to position the back stop element in a vertical status, while the back stop element also squeezes and presses the resetting block, the resetting elastic element and the sleeve block located on the other side, allowing the sleeve block to squeeze and press the pushing element so as to position the pushing element in a vertical status; at this moment, the pushing shaft designed for preventing backward movement can be released for refilling the syringe, and after completing the refilling process, the release elastic element and the resetting elastic element are automatically reset by elastic force, so that the back stop element or the pushing element can present an inclined status once again.

In a preferred embodiment, the abutting blocks are configured to have a plurality of different lengths and collectively installed in a stroke control mechanism which is set up on the outer case and has a rotating block located inside of the outer case, and such abutting blocks are evenly installed on the outside of the rotating block which is provided with an inner axle, and the inner axle penetrates through the outer case and extends to configure a control disc at the exterior, and one side of the control disc is installed with a snap elastic element, and the outer surface of the second case is provided with a plurality of fixation holes around the center of the inner axle, and the snap elastic element can be stuck and fixed in one of the fixation holes at a predetermined angle.

In a preferred embodiment, the control disc shows a number of segments for controllable strokes.

In a preferred embodiment, the number of abutting blocks, the number of segments and the number of fixation holes are equal.

In a preferred embodiment, the number of segments is four, and the lengths of the abutting blocks are respectively configured to 0.6 mm, 0.4 mm, 0.3 mm and 0.24 mm.

The present invention is illustrated but not limited by the following embodiments and drawings.

DETAILED DESCRIPTION OF THE PREFERRED EMBODIMENTS

Figure 1:
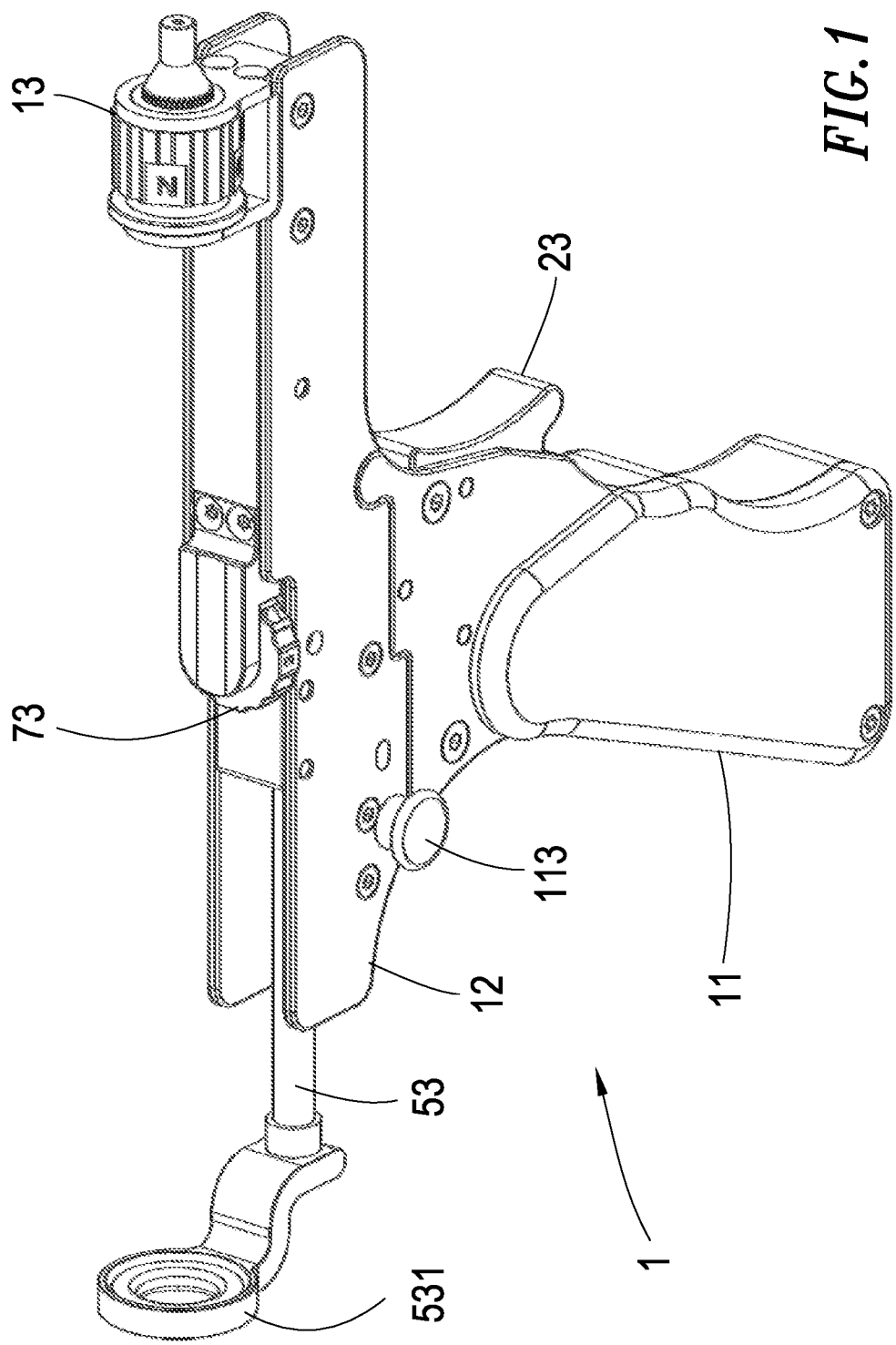
FIG. 1 shows a perspective stereo view of the electric injection device according to the present invention.

Other technical contents, aspects and effects in relation to the present invention can be clearly appreciated through the detailed descriptions concerning the preferred embodiments of the present invention in conjunction with the appended drawings.

It should be appreciated that the term "on" used to describe the position of the structure disclosed in the contents of the present specification refers to any surface position of the structure, not commonly known as the directional terms, e.g., "on top of", "above", etc. Meanwhile, the terms "above" and "below" used to describe the position of the structure refer to the directionality of the position of the structure under common usage.

Moreover, it should be understood that the terms "inner side" and "inside" disclosed in the description of the present invention for illustrating a structural position refer to being close to the central position of the structure body, or a non-exposed position in use; the term "inward" refers to facing close to the central position of the structure body, or facing a non-exposed position in use; the terms "outer side" and "outside" refer to being away from the central position of the structure body, or an exposed position in use; and the term "outward" refers to facing away from the central position of the structure body, or facing an exposed position in use.

In addition, the terms "fixedly provided", "installed", "wrapped around", "arranged" or "set up" disclosed in the contents of the present specification for describing the combination relationship of the structure generally refer to that multiple structures will not easily fall apart or drop down after combination processes, and such connections or combinations may comprise a fixed connection, a detachable connection, or otherwise an integrally formed connection; also, it may be a mechanical connection or an electrical connection; besides, it may be a directly physical connection or an indirectly physical connection through an intermediate medium, or otherwise an internal connection of two elements by using, e.g., threads, latches, fasteners, nails, adhesives or high frequency waves or any other feasible approaches, and the terms "wrapped around" or "sleeved" indicate that one structures is combined on the outside of the other structure.

Also, the terms "connected" or "electrically connected" disclosed in the contents of the present specification for describing the structural combination relationship refer to the combination of electric power enabling or network communications by using e.g., wires, circuit boards, network cables, Bluetooth or wireless networks or any other feasible approaches.

Besides, the term "pivotally installed" disclosed in the description of the present invention for illustrating the structural combination relationship refers to the arrangement of multiple structures by means of a combination of any two of, e.g., a hinge, a column, a sphere, a hole, or a groove, or otherwise between multiple structures via matching bearings for mutual assemblage such that the assembled multiple structures can still arbitrarily rotate or slide within a restricted range without being separated, detached or dropped easily.

Moreover, the term "formed" or "extended" disclosed in the description of the present invention for describing the structural combination relationship generally refer to a single structure or multiple structures which are combined into one single body during the manufacture procedure, or alternatively the corresponding structure on the same body which is generated due to different positions, shapes and functions.

Now, please refer to FIG. 1 which shows the electric injection device comprises an outer case 1, a drive mechanism 2, a transmission mechanism 3, a linkage mechanism 4 and a push mechanism 5.

In FIG. 1, the outer case is designed to be gun-shaped and includes a first case 11 and a second case 12, in which the first case 11 is installed under the second case 12 for hand-holding operations, and a syringe head base 13 is installed on the second case 12.

Figure 2:
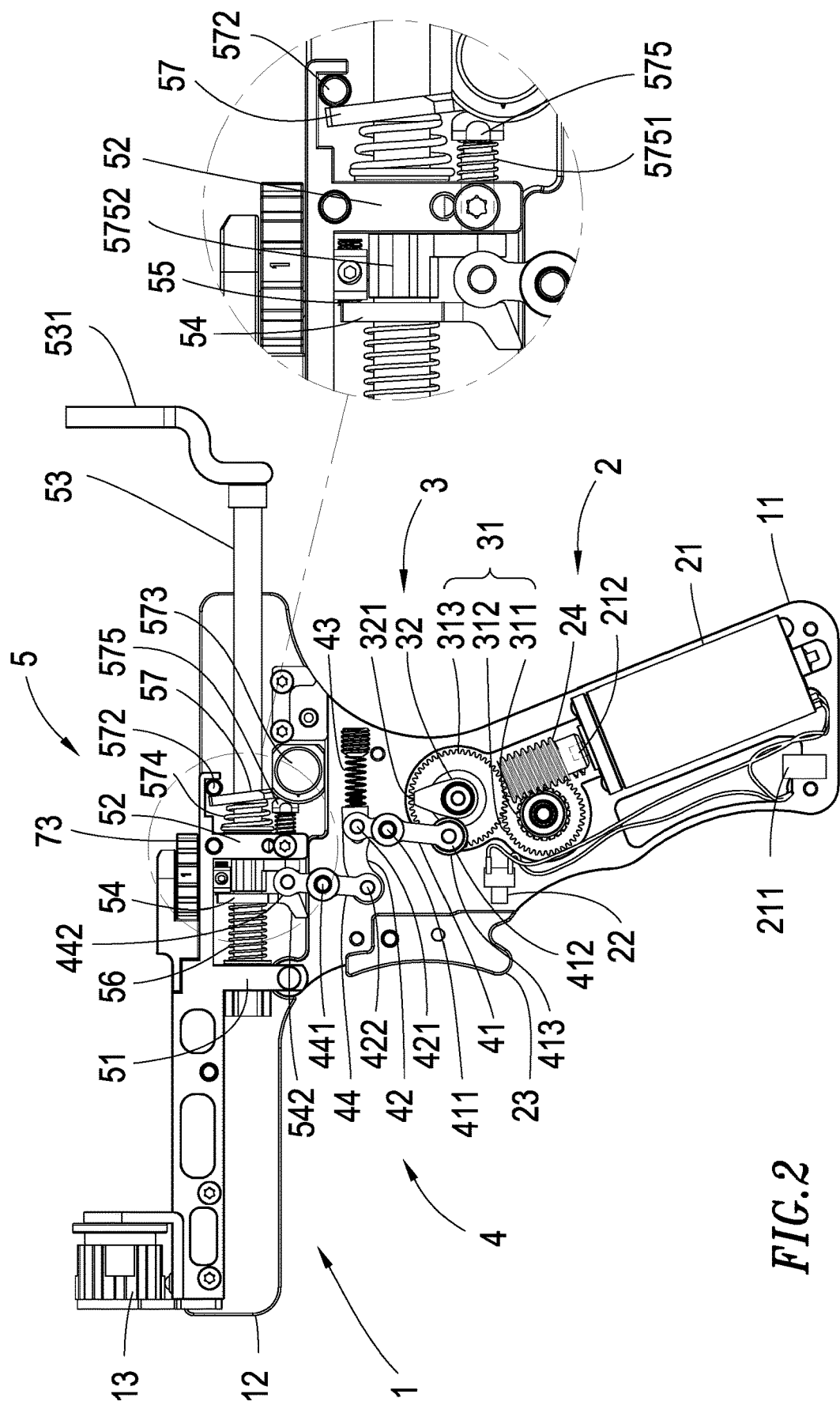
FIG. 2 shows a planar view for the front inner structure of the electric injection device according to the present invention.
Figure 3:
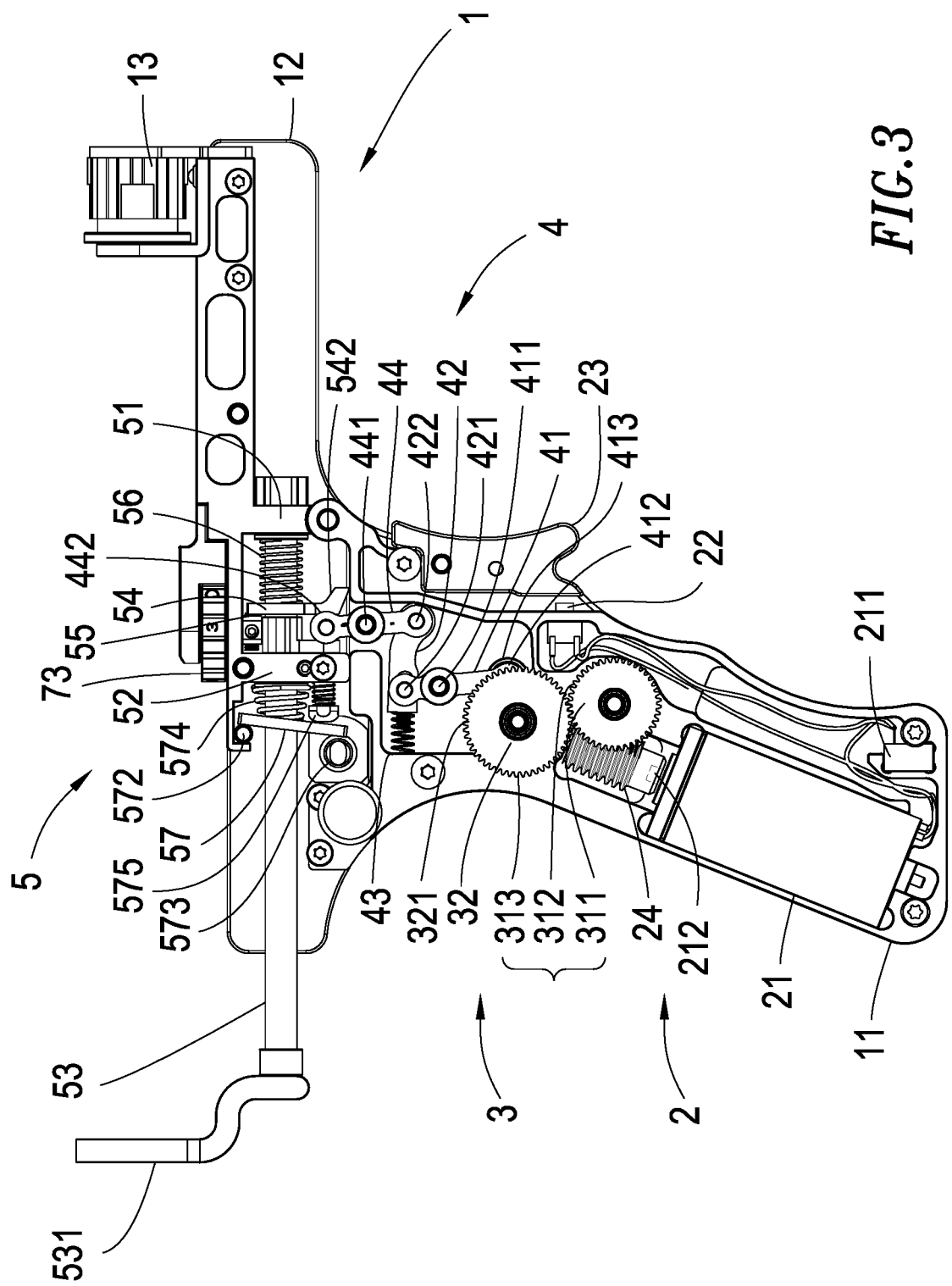
FIG. 3 shows a planar view for the rear inner structure of the electric injection device according to the present invention.

Next, refer to FIGS. 2 and 3, the drive mechanism 2 is installed inside the first case 11 and has a drive motor 21 which is electrically connected to a switch 22. A touch component 23 exposed to the outside of first case 11 is installed besides the switch 22. The touch component 23 can be touched or pressed by a finger when a hand holds the first case 11 so that the touch component 23 can hit the switch 22 to further activate the drive motor 21. The required power of the drive motor 21 can be supplied by electrically connecting to the power grid or a battery 211.

Further, the drive motor 21 has a rotation axle 212, and a drive gear block 24 is installed on the rotation axle 212, so that the rotation axle 212 can be rotated after activating the drive motor 21 and the power can be transmitted through the drive gear block 24.

Please refer to FIGS. 2 and 3, it can be observed that the transmission mechanism 3 is installed inside the first case 11 and includes a gear set 31 meshing with the drive gear block 24, and the gear set 31 is fixedly provided with a push block 32, and one end of the push block 32 has a protrusion 321, thereby allowing the drive gear block 24 to drive the gear set 31 and make the push block 32 rotate regularly. One example of the drive gear block 24 is a worm gear, and one example of the push block 32 is a cam.

Here, the gear set 31 is configured with a first gear 311, a second gear 312 and a third gear 313. When the drive gear block 24 is a worm gear, then the first gear 311 is a worm wheel. The first gear 311 meshes with the drive gear block 24 and the first gear 311 and the second gear 312 are configured to be coaxial, and the number of teeth and outer diameter of the first gear 311 are both smaller than those of the second gear 312. Besides, the second gear 312 meshes with the third gear 313 and the third gear 313 and the push block 32 are configured to be coaxial. In this way, the first gear 311 is driven by the drive gear block 24 so that it rotates together with the coaxial second gear 312. Then, the third gear 313 is driven by the second gear 312 so that it rotates together with the coaxial push block 32. In addition, the first gear 311 allows the second gear 312 having a larger number of teeth and a larger outer diameter to coaxially rotate with it, thus effectively reducing the speed and increasing the torque originally output from the drive motor 21.

Figure 14:
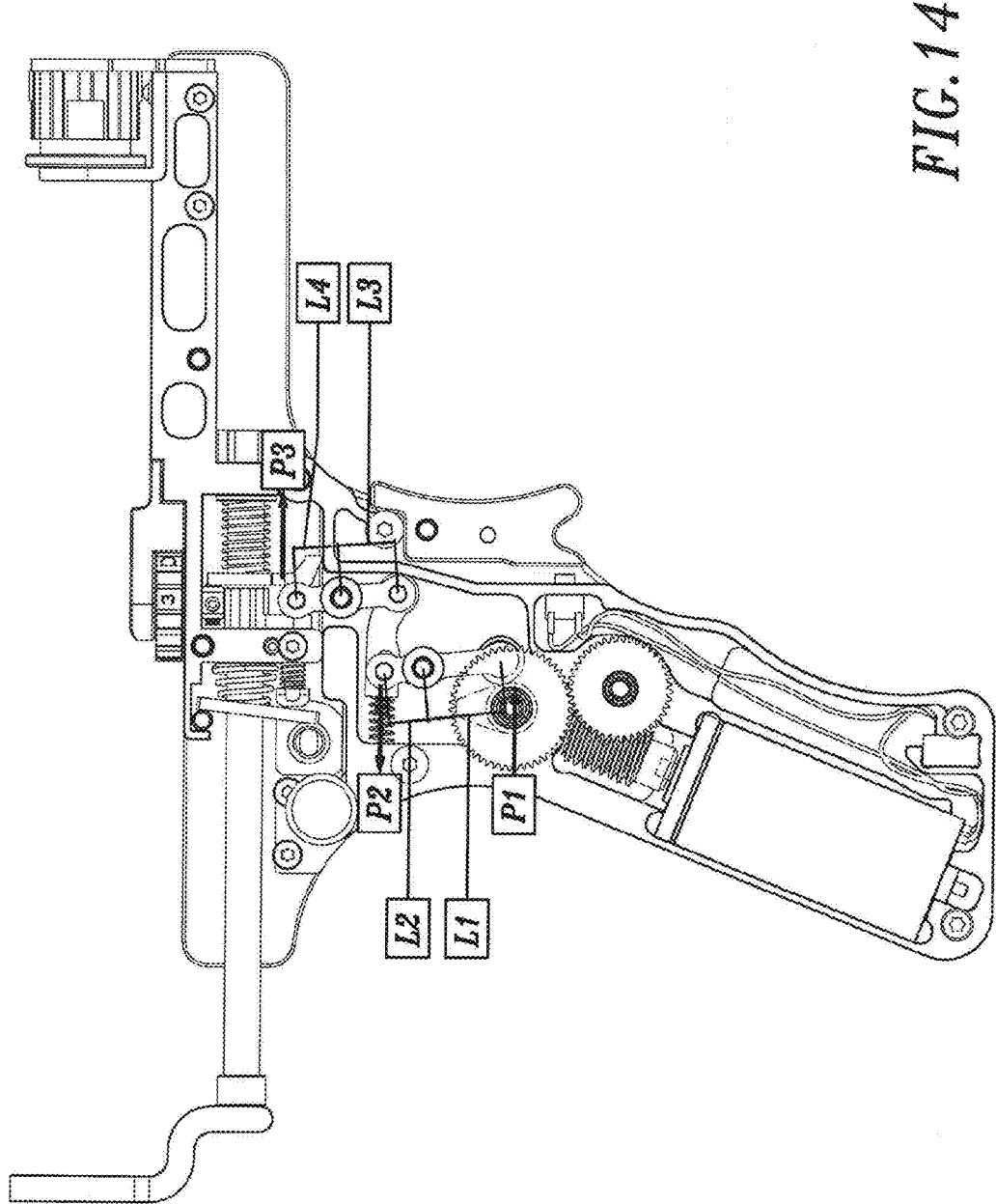
FIG. 14 shows the planar view for the rear inner structure of the electric injection device in FIG. 3, in which distances L1, L2, L3 and L4 are labeled.

Referring continuously to FIGS. 2 and 3, it can be appreciated that the linkage mechanism 4 is installed inside the first case 11 and includes a first linkage rod 41, a reciprocating linkage rod 42, a reciprocating elastic element 43 and a second linkage rod 44. The first linkage rod 41 is provided with a first fulcrum 411, and one end of the first linkage rod 41 is served as a swing end 412. The first fulcrum 411 is pivotally installed at a position on the inner side of the first case 11 close to the push block 32 such that the swing end 412 corresponds in adjacent to the push block 32. Additionally, a first pivot point 421 and a second pivot point 422 are respectively installed at the positions close to the two ends of the reciprocating linkage rod 42. The other end of the first linkage rod 41 away from the swing end 412 is pivotally installed to the first pivot point 421, and the reciprocating elastic element 43 is set up beside the first pivot point 421 and uses a compression spring. The two ends of the reciprocating elastic element 43 are respectively pressed against the inner side of the first case 11 and beside the first pivot point 421 of the reciprocating linkage rod 42. Moreover, the second linkage rod 44 is provided with a second fulcrum 441, and one end of the second linkage rod 44 is configured as a brake end 442 which is exposed to the outside of the first case 11 and extends to the inside of the second case 12, while the other end of the second linkage rod 44 away from the brake end 442 is pivotally installed to the second pivot point 422. As shown in FIG. 14, the distance L1 from the swing end 412 to the first fulcrum 411 is longer than the distance L2 from the first fulcrum 411 to the first pivot point 421 of the reciprocating linkage rod 42, and the distance L3 from the second pivot point 422 of the reciprocating linkage rod 42 to the second fulcrum 441 is longer than the distance L4 from the second fulcrum 441 to the brake end 442. Since the distance L1 is longer than the distance L2, when a force P1 is applied to the swing end 412, the structure of the first linkage rod 41 causes a corresponding force P2 to be generated at the first pivot point 421, such that the force P2 is greater than the force P1 (because P1×L1=P2×L2). Similarly, since the distance L3 is longer than the distance L4, when the force P2 is generated at the first pivot point 421, the force P2 is transmitted through the reciprocating linkage rod 42 and is thus also applied to the second pivot point 422, and the structure of the second linkage rod 44 causes a corresponding force P3 to be generated at the brake end 442, such that the force P3 is greater than the force P2 (because P2×L3=P3×L4). Therefore, the linkage mechanism 4 allows the force as well as the power to increase.

Figure 4:
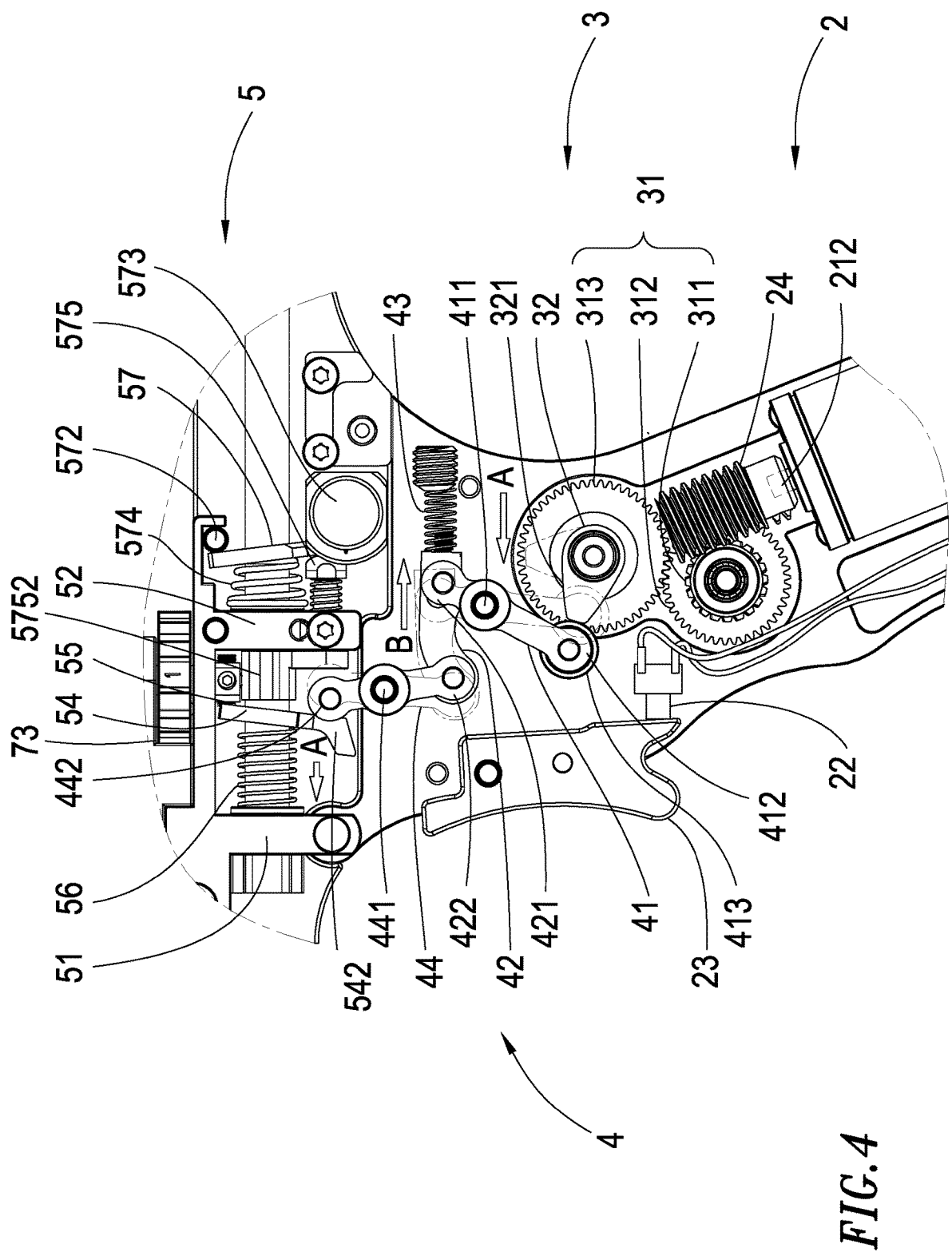
FIG. 4 shows a local planar view for the implemented transmission structure of the electric injection device according to the present invention.
Figure 5:
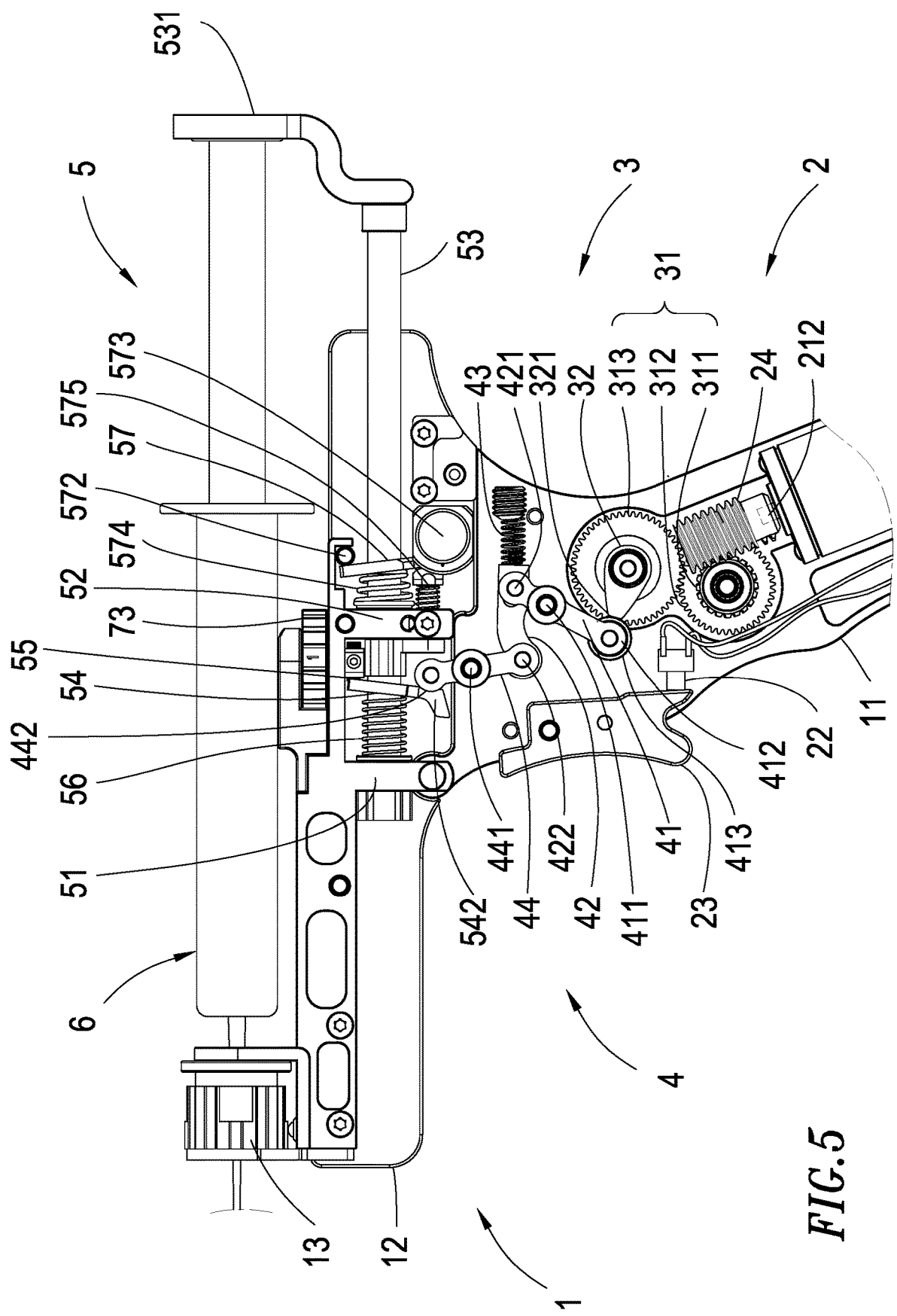
FIG. 5 shows a local planar view for the implemented injection operation of the electric injection device according to the present invention.

Referring to FIGS. 3-5, herein, the protrusion 321 can dial and push the swing end 412 when the push block 32 rotates so that the swing end 412 swings in a circular-arc fashion by using the first fulcrum 411 as the axle center towards a first direction A. The first pivot point 421 on the other end operates in conjunction with the reciprocating linkage rod 42 towards a second direction B opposite to the first direction A when the swing end 412 swings, thus compressing the reciprocating elastic element 43. Simultaneously, the reciprocating linkage rod 42 brings the second pivot point 422 to swing in a circular-arc way by using the second fulcrum 441 as the axle center towards the second direction B, while the brake end 442 on the other end moves towards the first direction A opposite to the second direction B. Then, the reciprocating elastic element 43 automatically resets its position by means of the elastic force when the protrusion 321 rotates and detaches from the swing end 412 so that the reciprocating linkage rod 42 drives the second pivot point 422 to perform reciprocating swing movements by using the second fulcrum 441 as the axle center, while the brake end 442 on the other end also returns back.

Subsequently, the swing end 412 will present a short, temporary standstill condition (the protrusion 321 is away from the swing end 412 at this moment) during a period which is after the swing end 412 separates from the protrusion 321 and before the protrusion 321 pushes the swing end 412 again. Assuming the protrusion 321 occupies approximately ⅓ of the outer diameter of the push block 32, the remaining ⅔ will leave the swing end 412 in a standstill condition. As a result, the brake end 442 follows an average rotation speed of the rotated protrusion 321 driven by the push block 32 to continuously conduct a reciprocating motion including moving and resting actions. Herein, a pulley 413 is pivotally installed on the swing end 412. When the protrusion 321 dials and pushes the swing end 412, the pulley 413 can be pushed to become idling and the protrusion 321 detaches successfully, thereby ensuring great fluency of movement between such elements.

Figure 6:
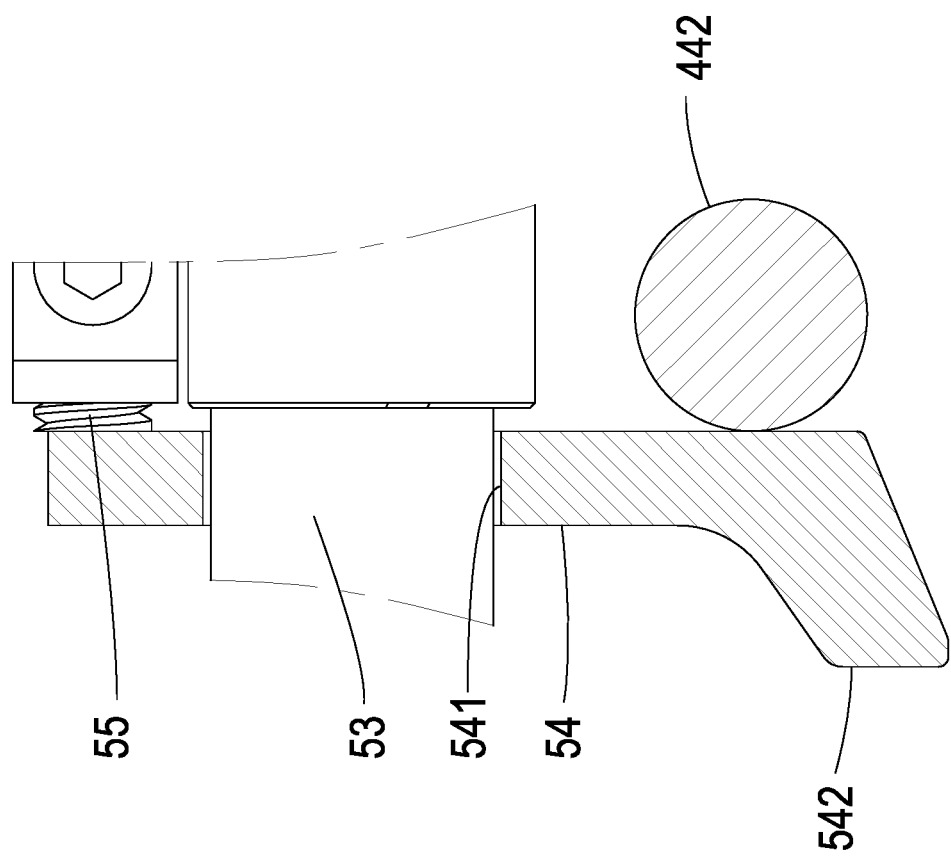
FIG. 6 shows a local cross-sectional view for the pushing element structure of the electric injection device according to the present invention.
Figure 7:
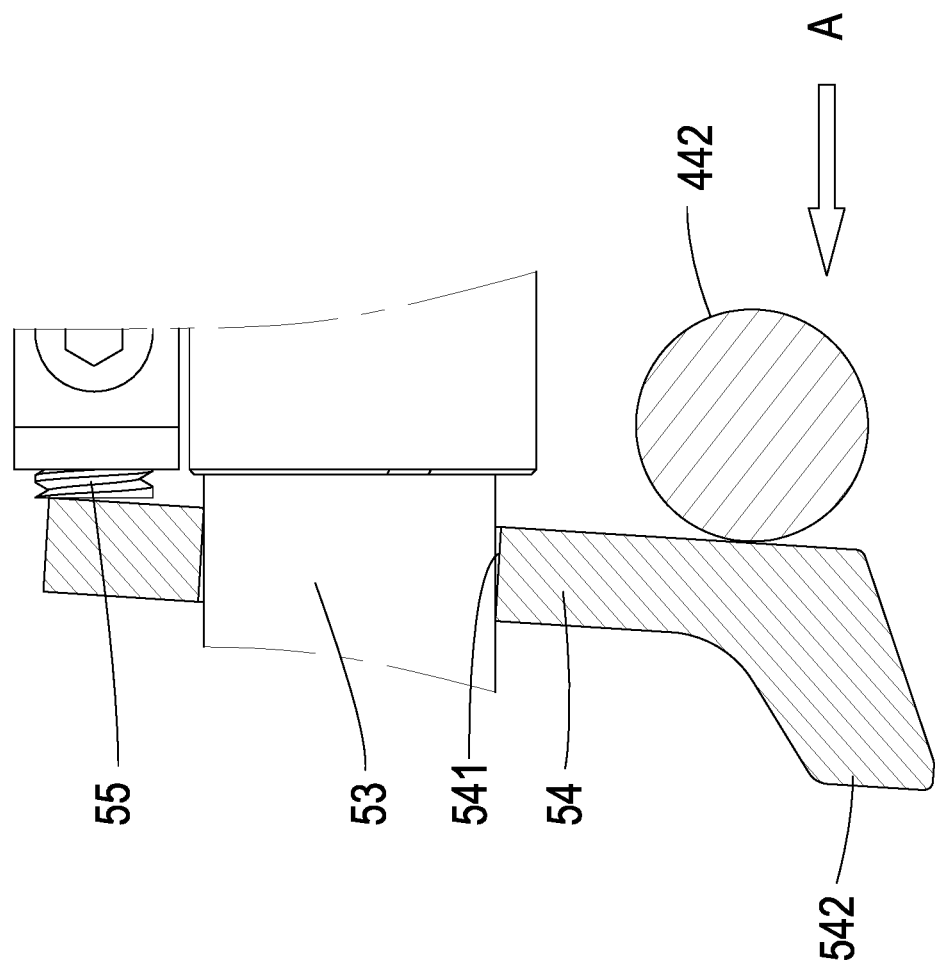
FIG. 7 shows a local cross-sectional view for the pushing element implemented push operation of the electric injection device according to the present invention.

Referring next to FIGS. 2, 3 and 6, it can be understood that the push mechanism 5 is installed inside the second case 2 and includes a first stop block 51, a second stop block 52, a pushing shaft 53 and a pushing element 54, wherein the first stop block 51 and the second stop block 52 are parallel to each other and stably installed on the inner side of the second case 12, and the first stop block 51 and the second stop block 52 may be also integrally formed inside the second case 12. The pushing shaft 53 passes through the first stop block 51 and the second stop block 52 at the same time, the pushing element 54 has a hole 541 so that the pushing element 54 may wrap around the pushing shaft 53 via the hole 541 and correspond to the position between the brake end 442 and the first stop block 51. The outer side of the pushing element 54 is further formed with a push end 542 extending next to the brake end 442. One or more abutting blocks 55 are also installed inside the second case 12 so that the abutting block 55 and brake end 442 are both located on the same side of the pushing element 54 and the abutting block 55 is located above the brake end 442. In addition, a first abutting elastic element 56 which is wrapped around the pushing shaft 53 and could be a compression spring is located on the other side of the pushing element 54, while two ends of the abutting elastic element 56 respectively abut against the pushing element 54 and one side of the first stop block 51 in order to push the pushing element 54 against the abutting block 55 and the brake end 442.

In FIGS. 4-7, the outer diameter of the hole 541 is larger than that of the pushing shaft 53. When the brake end 442 moves towards the first direction A, the push end 542 will be pushed such that the lower part of the pushing element 54 pushes and presses against the first abutting elastic element 56 in the first direction A, thus making the pushing element 54 inclined. During such inclination, the upper and lower edges of the hole 541 will firstly abut against the upper and lower surfaces of the pushing shaft 53. As the inclination angle increases, the upper and lower edges of the hole 541 can clamp the upper and lower surfaces of the pushing shaft 53 to move. Then, the pushing shaft 53 can be driven to move in the first direction A when the pushing element 54 is continuously pushed. Since the brake end 442 performs regular and continuous reciprocating movements, the pushing shaft 53 can be continuously driven to move towards the first direction A.

Additionally, a pressure board 531 can be provided at the end of the pushing shaft 53 and a syringe 6 can be placed between the syringe head base 13 and the pressure board 531. Therefore, when the pushing shaft 53 is continuously pushed, the pressure board 531 can incessantly press the syringe 6 to achieve the intended automatic injection effect.

Figure 8:
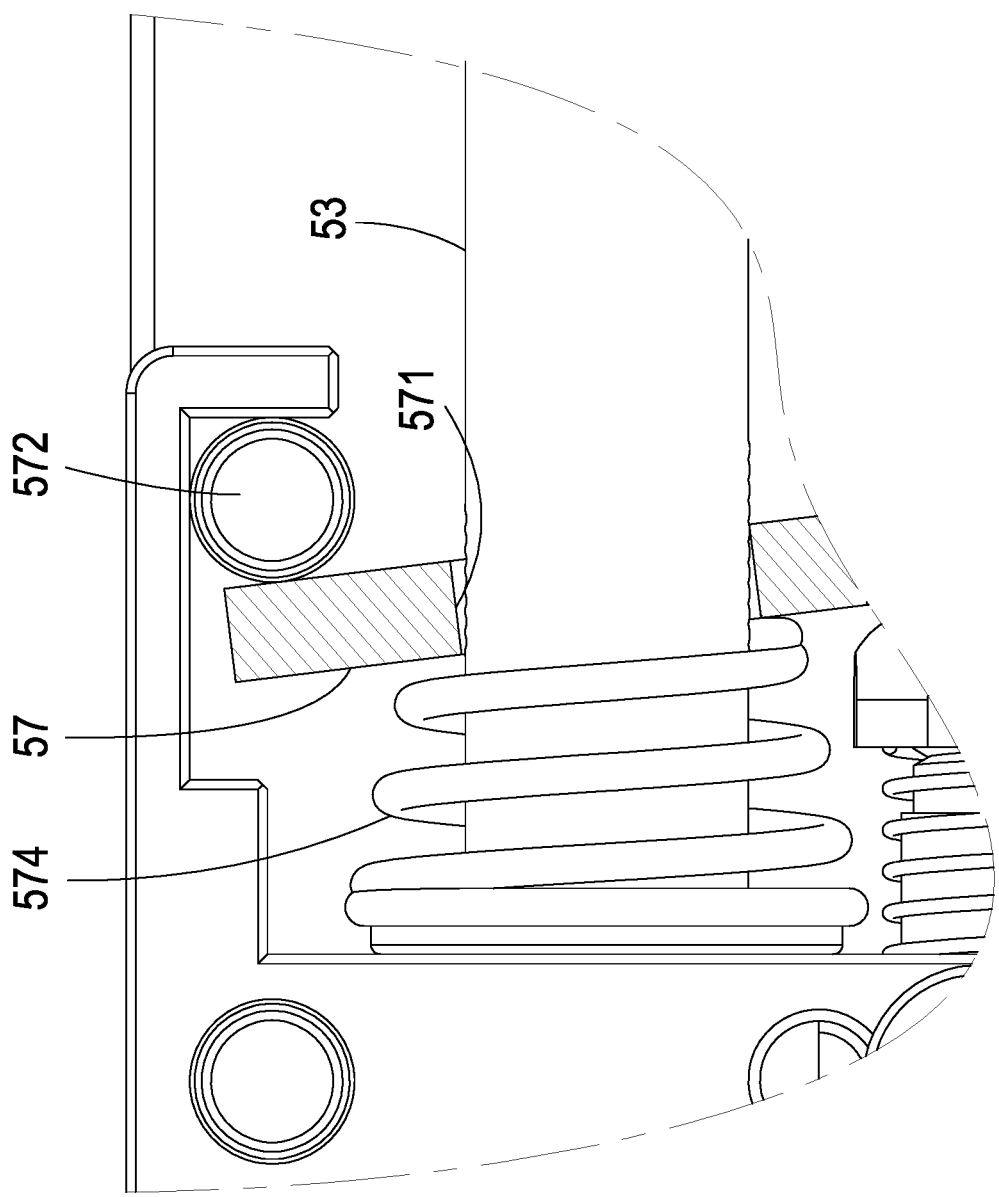
FIG. 8 shows a local cross-sectional view for the back stop element structure of the electric injection device according to the present invention.
Figure 9:
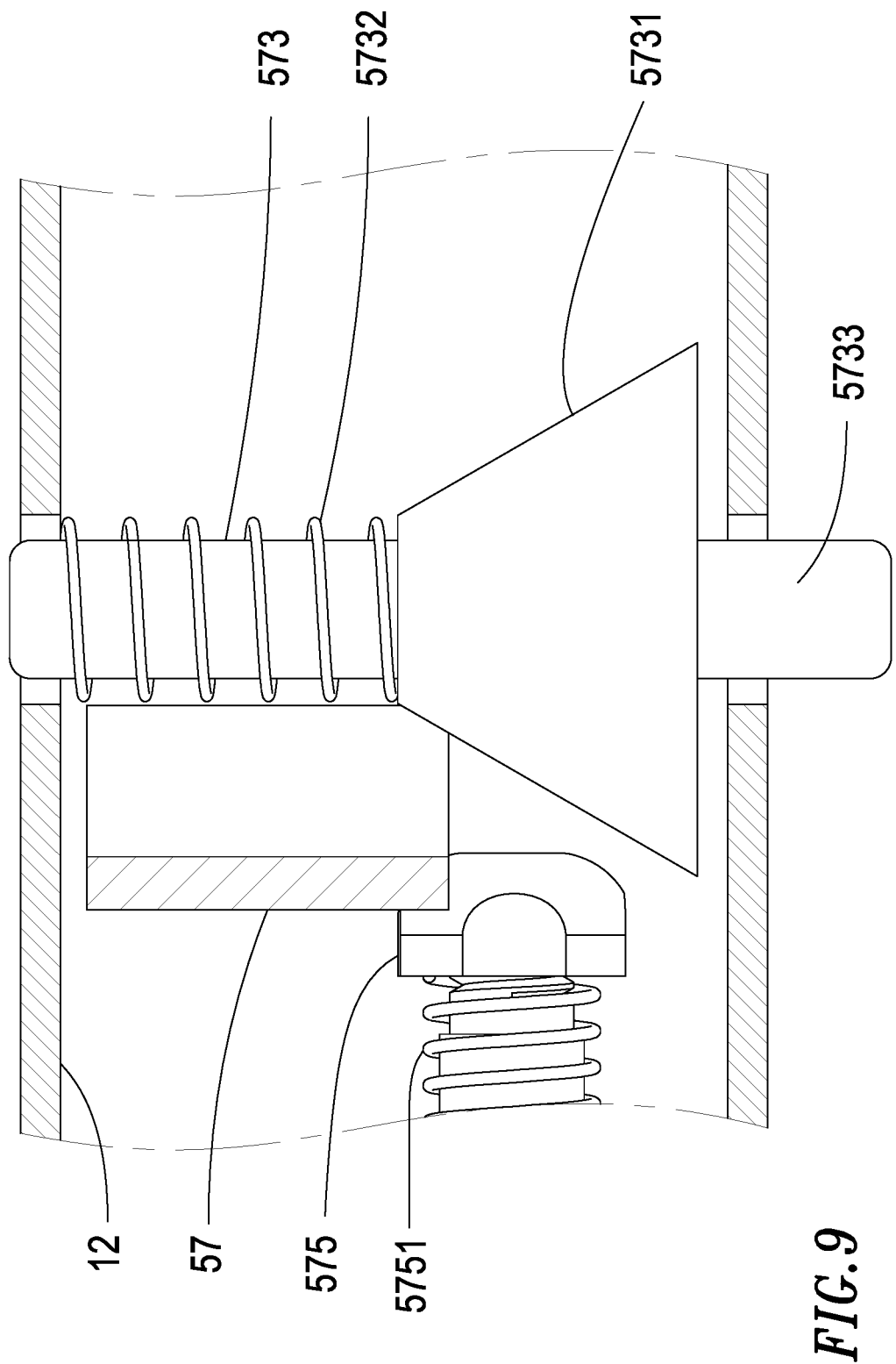
FIG. 9 shows a local cross-sectional view for the release blockage structure of the electric injection device according to the present invention.
Figure 10:
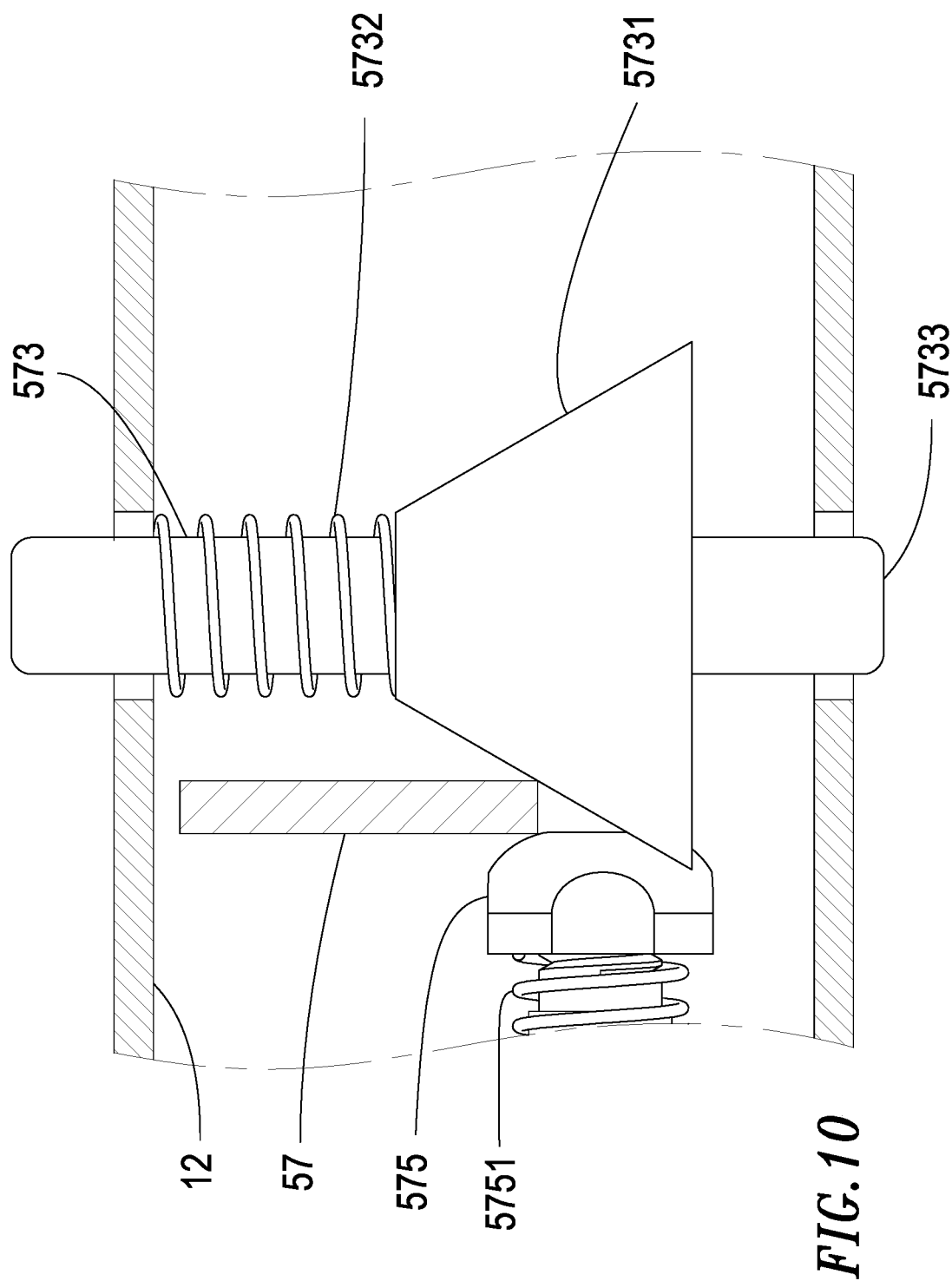
FIG. 10 shows a local cross-sectional view for the release blockage implemented release operation of the electric injection device according to the present invention.

Subsequently, referring to FIGS. 2, 8 and 9, a back stop element 57 which includes a back stop hole 571 is provided and wrapped around the pushing shaft 53 via the back stop hole 571 correspondingly between the pressure board 531 and the second stop block 52. The inside of the outer case 12 is also installed with a back stop fulcrum 572 and a release blockage 573 which are respectively located on the same side of the back stop element 57 and the back stop fulcrum 572 is located above the release blockage 573. In addition, a second abutting elastic element 574 wrapped around the pushing shaft 53 and a resetting block 575 positioned under the second abutting elastic element 574 which could be a compression spring are provided on the other side of the back stop element 57. The two ends of the second abutting elastic element 574 respectively abut against the back stop element 57 and one side of the second stop block 52, thereby pushing the back stop element 57 against the back stop fulcrum 572 and the release blockage 573 and allowing tilting the back stop element 57. When the back stop element 57 is in an inclination state, it is possible to prevent the pushing shaft 53 from retreating towards the direction of the pressure board 531.

Moreover, referring to FIGS. 2, 8-10, it can be observed that the release blockage 573 further comprises an oblique plane 5731, a release elastic element 5732 and a button 5733 exposed to the outside of the second case 12. The narrower part of the oblique plane 5731 is for the back stop element 57 to abut and push against, the release elastic element 5732 could be a compression spring and the two ends thereof respectively abut against the inner side of the second case 12 and one end of the oblique plane 5731. The resetting block 575 includes a resetting elastic element 5751 and extends to a sleeve block 5752, in which a compression spring is used as the resetting elastic element 5751. Two ends of the resetting elastic element 5751 respectively abut against the resetting block 575 and one side of the second stop block 52. The sleeve block 5752 goes through the second stop block 52 and is sleeved on the pushing shaft 53 between the second stop block 52 and the pushing element 54. Therefore, after pressing down the button 5733, the oblique plane 5731 can squeeze and press the release elastic element 5732, thereby making the back stop element 57 push against the wider part of the oblique plane 5731 to position the back stop element 57 in a vertical status, while the back stop element 57 also squeezes and presses the resetting block 575, the resetting elastic element 5751 and the sleeve block 5752 located on the other side, allowing the sleeve block 5752 to squeeze and press the pushing element 54 so as to position the pushing element 54 in a vertical status. At this moment, the pushing shaft 53 designed for preventing backward movement can be released and exited for refilling the syringe 6. After completing the refilling process, the release elastic element 5722 and the resetting elastic element 5751 are automatically reset by elastic force, so that the back stop element 57 or the pushing element 54 can present an inclined status once again.

Figure 11:
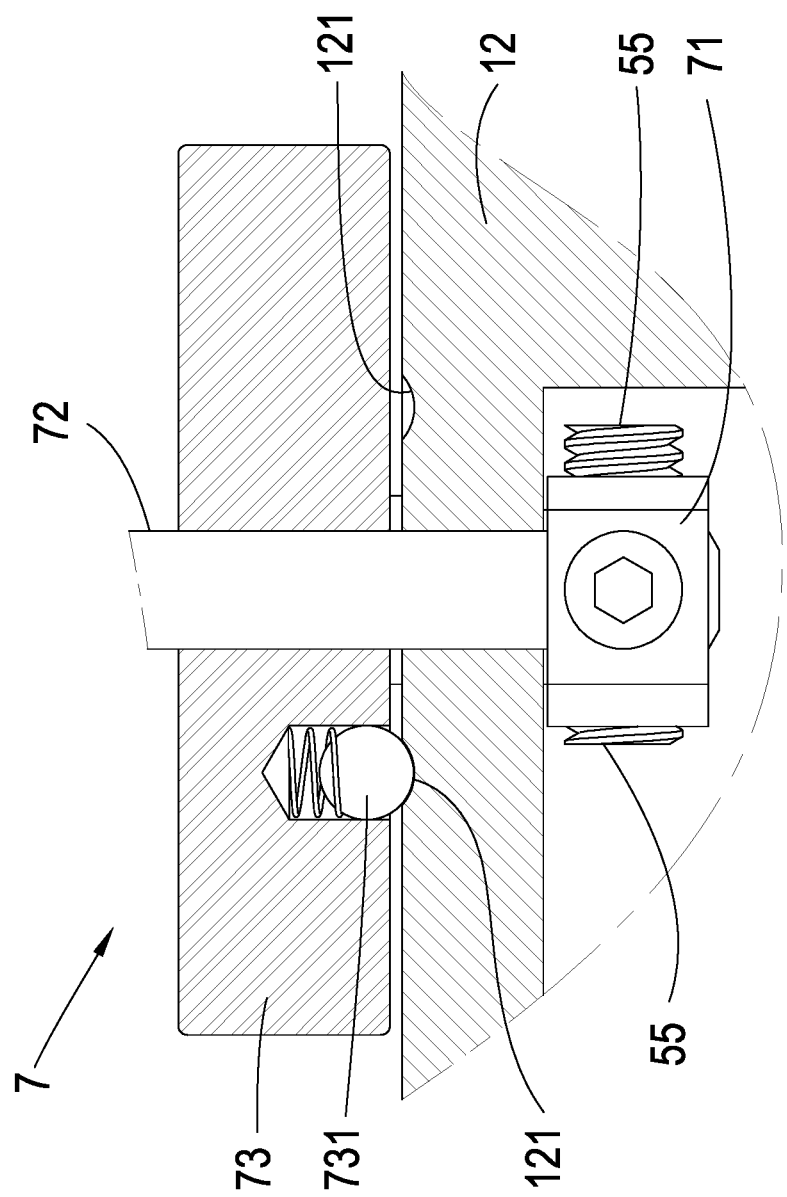
FIG. 11 shows a local cross-sectional view for the stroke control mechanism of the electric injection device according to the present invention.
Figure 12:
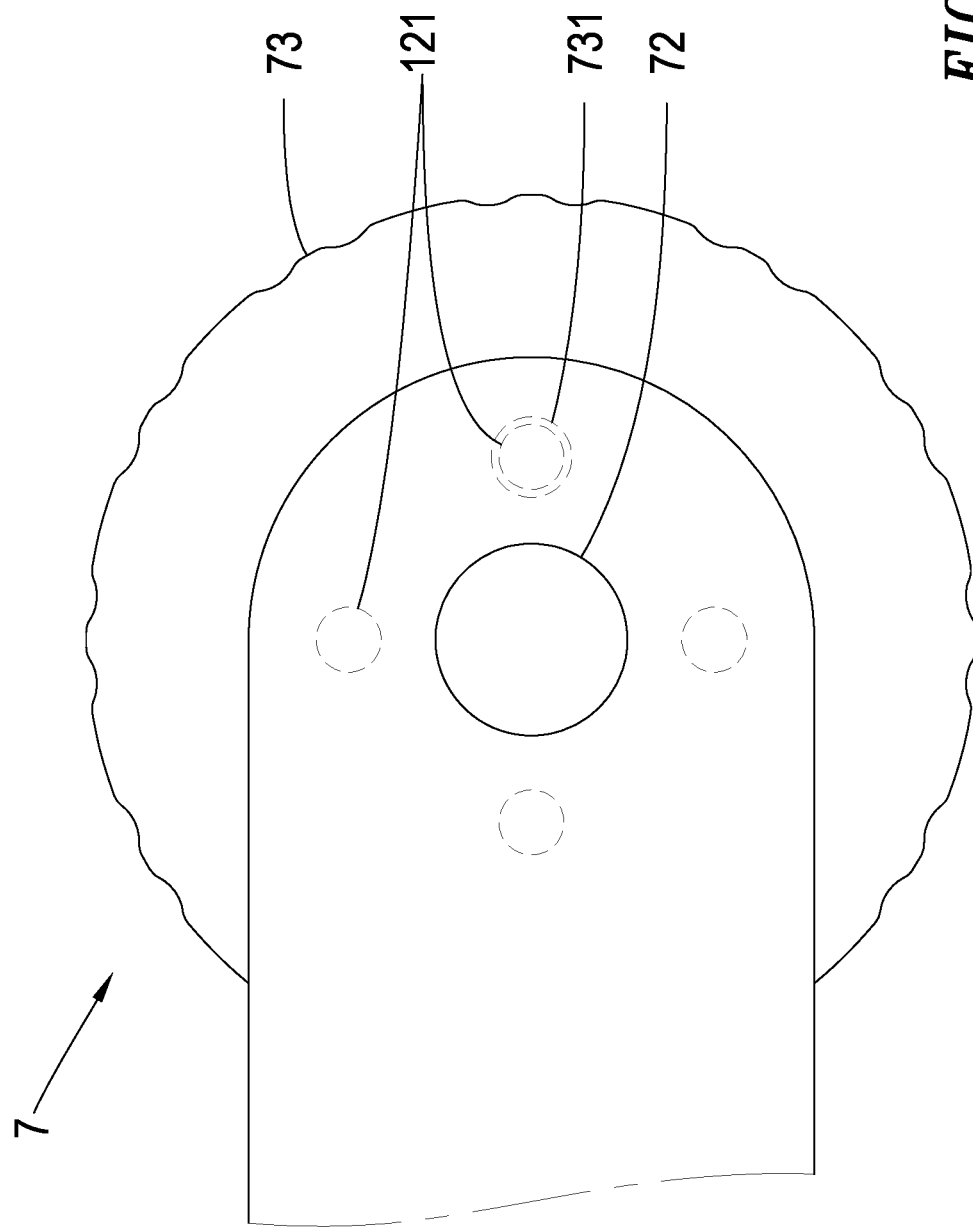
FIG. 12 shows a planar view for the stroke control mechanism of the electric injection device according to the present invention.

Referring to FIGS. 2, 11 and 12, the abutting blocks 55 may have different lengths, so it is possible to change the wagging stroke distance of the pushing element 54 each time which is caused by the brake end 442 pushing the push end 542 (in the present embodiment, the longer the abutting block 55 is, the shorter the distance that the brake end 442 pushes the push end 542 is; on the contrary, the shorter the abutting block 55 is, the longer the distance that the brake end 442 pushes the push end 542 is). As a result, the plurality of abutting blocks 55 may be designed with different lengths and collectively set up in a stroke control mechanism 7 which can be installed on the second case 12 and includes a rotating block 71 located inside the second case 12. Such abutting blocks 55 are evenly located on the outer side of the rotating block 71. Besides, an inner axle 72 in the second case 12 is stably installed on the rotating block 71 and extends to the outside of the second case 12. A control disc 73 is stably installed on the outside of the second case 12 and capable of showing the number of segments, and one side of the control disc 73 is set up with a snap elastic element 731, the outer surface of the second case 12 is provided with a plurality of fixation holes 121 around the center of the inner axle 72, and the snap elastic element 731 can be stuck and fixed in one of the fixation holes 121 at a predetermined angle.

Herein it should be noticed that the number of the abutting blocks 55 and the number of the segments are configured to be the same with the number of the fixation holes 121. If it is intended to include four segments, the control disc 73 will show 1-4 segments by setting each 90° (i.e., 360°/4) as a division for every segment, and one fixation hole 121 will be configured at each 90° by taking the inner axle 72 as the center. In addition, four abutting blocks 55 will installed and have different lengths, so that the snap elastic element 731 will be snapped and fixed into the next fixation hole 121 when the control disc 73 rotates 90°. Then, one of the abutting blocks 55 will abut against the pushing element 54, thereby allowing each of the abutting blocks 55 with different lengths to control the oscillating stroke distance of the pushing element 54. For example, if the length of the abutting block 55 is 0.6 mm, then each injection is (1/100) cc; if the length of the abutting block 55 is 0.4 mm, then each injection is (1/150) cc; if the length of the abutting block 55 is 0.3 mm, then each injection is (1/200) cc; if the length of the abutting block 55 is 0.24 mm, then each injection is (1/250) cc.

Figure 13:
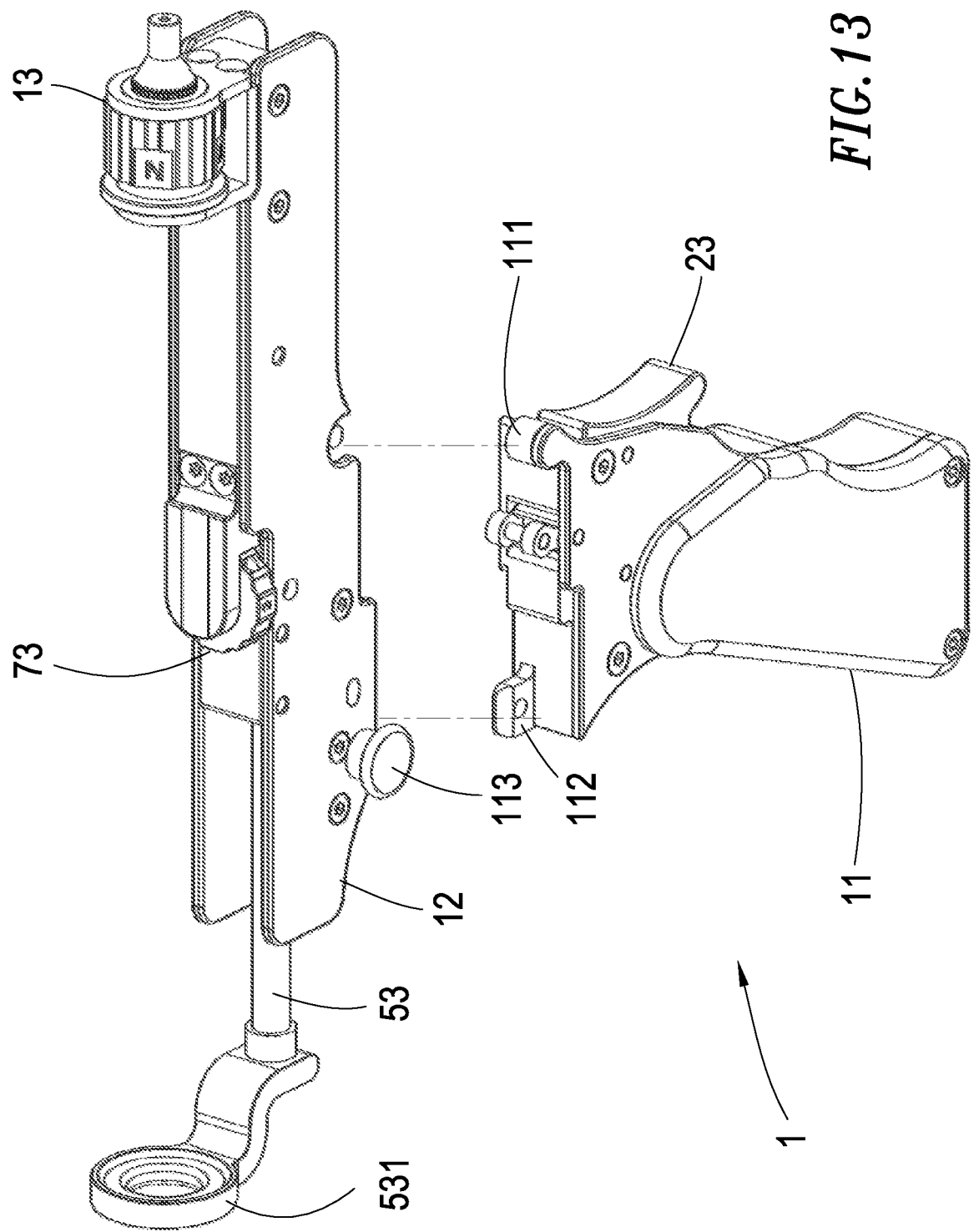
FIG. 13 shows an outer case disassembled stereo view of the electric injection device according to the present invention. p

Furthermore, referring to FIG. 13, it can be seen that the two ends of the junctions between the first case 11 and the second case 12 are respectively installed with a pivot end 111 and a locking end 112. The pivot end 111 is applied to pivotally connect to the second case 12, while the locking end 112 is stably locked to the second case 12 by means of a locking element 113. The pivot end 111 can be dismantled from the second case 12 after releasing the locking element 113, thereby further disassembling the first case 11 and the second case 12 so as to facilitate independent disinfection or cleaning processes on the second housing 12.

The previously disclosed embodiments are merely illustrative of some preferred ones of the present invention, which are not intended to limit the scope thereof. Those who are skilled in the relevant technical fields can, after understanding the technical features and embodiments of the present invention as explained hereinabove, certainly make equivalent changes, alterations or modifications without departing from the spirit and scope of the present invention, which are nonetheless deemed as falling within the coverage of the present invention. Accordingly, the scope of the present invention to be protected by patent laws is subject to the definition of the claims attached to this specification.

What is claimed is:

1. An electric injection device, comprising:
an outer case comprising a first case, a second case and a syringe head base, in which the first case is installed under the second case for hand holding, and the syringe head base is installed outside the second case, wherein the first case and the second case can be arbitrarily disassembled, wherein the first case is arranged vertically and the second case is arranged horizontally so that the outer case is gun-shaped, wherein the first case and the second case are respectively installed with a pivot end and a locking end, and the pivot end is applied to pivotally connected to the second case, while the locking end is locked to the second case by means of a locking element, the pivot end can be dismantled from the second case after releasing the locking element thereby disassembling the first case and the second case;
a drive mechanism, installed within the first case and including a drive motor and a drive gear block driven by the drive motor;
a transmission mechanism, installed within the first case and including a gear set meshing with the drive gear block and a push block driven by the gear set;
a linkage mechanism, installed within the first case and including a first linkage rod, a reciprocating linkage rod, a reciprocating elastic element and a second linkage rod, wherein a first fulcrum is installed on the first linkage rod, one end of the first linkage rod is configured as a swing end, the first fulcrum is pivotally installed on the inner side of the outer case and close to without being connected to the push block so that the swing end is located on the path where the push block rotates, the positions close to the two ends of the reciprocating linkage rod are respectively configured with a first pivot point and a second pivot point, the other end of the first linkage rob away from the swing end is pivotally installed to the first pivot point, and the reciprocating elastic element is installed beside the first pivot point, the two ends of the reciprocating elastic element respectively abut against the inner side of the outer case and beside the first pivot point of the reciprocating linkage rod, a second fulcrum is configured on the second linkage rod, and a brake end is installed on one end of the second linkage rod, the other end of the second linkage rod away from the brake end is pivotally installed to the second pivot point, and wherein the distance from the swing end to the first fulcrum is longer than the distance from the first fulcrum to the first pivot point of the reciprocating linkage rod, and the distance from the second pivot point of the reciprocating linkage rod to the second fulcrum is longer than the distance from the second fulcrum to the brake end, and when the push block rotates and pushes the swing end, the brake end performs reciprocating movements; and a push mechanism, installed within the second case and including a first stop block, a second stop block, a pushing shaft and a pushing element, in which the first stop block and the second stop block are installed parallel to each other on the inner side of the second case, the pushing shaft is installed through the first stop block and the second stop block at the same time, a pressure board is installed at the end of the pushing shaft so that a syringe can be installed between the syringe head base and the pressure board, and in which the pushing element has a hole for the pushing element to wrap around the pushing shaft via the hole correspondingly between the brake end and the first stop block, the outer side of the pushing element is further formed with a push end extending next to the brake end, the push end is applied to be pushed by the brake end thus further driving the pushing element, and one or more abutting blocks are installed inside the second case so that the one or more abutting blocks and the brake end are respectively located on the same side of the pushing element, wherein a first abutting elastic element wrapped around the pushing shaft is located on the other side of the pushing element, and the two ends of the first abutting elastic element respectively abut against the pushing element and one side of the first stop block thereby pushing the pushing element against the one or more abutting blocks and the brake end, and the outer diameter of the hole on the pushing element is larger than that of the pushing shaft such that the pushing element will become inclined when the brake end pushes the pushing element, and, during such an inclination condition, the upper and lower edges of the hole will clamp the upper and lower surfaces of the pushing shaft to move, and then the pushing shaft can be driven to push in one direction when the pushing element is continuously pushed, so that the continuous reciprocating action of the brake end makes the pushing shaft drive the pressure board to continuously press the syringe, wherein a back stop element which includes a back stop hole is provided and wrapped around the pushing shaft via the back stop hole correspondingly between the pressure board and the second stop block, and the inside of the outer case is also installed with a back stop fulcrum and a release blockage which are respectively located on the same side of the back stop element; in addition, wherein a second abutting elastic element wrapped around the pushing shaft and a resetting block positioned under the second abutting elastic element are provided on the other side of the back stop element, wherein the two ends of the second abutting elastic element respectively abut against the back stop element and one side of the second stop block thereby pushing the back stop element against the back stop fulcrum and the release blockage and allowing tilting the back stop element.

2. The electric injection device according to claim 1, wherein the drive motor is electrically connected to a switch.

3. The electric injection device according to claim 2, wherein a touch component exposed to the outside of the outer case is installed beside the switch and is applied for hitting the switch so as to further activate the drive motor.

4. The electric injection device according to claim 1, wherein the drive motor is electrically connected to a power grid or a battery.

5. The electric injection device according to claim 1, wherein the gear set is configured with a first gear, a second gear and a third gear, and the first gear meshes with the drive gear block, the first gear and the second gear are configured to be coaxial, the second gear meshes with the third gear, the third gear and the push block are set to be coaxial, and the drive gear block drives the first gear such that the coaxial second gear rotates accordingly thereby allowing the second gear to drive the third gear to rotate the coaxial push block.

6. The electric injection device according to claim 5, wherein the number of teeth and the outer diameter of the first gear are both smaller than those of the second gear.

7. The electric injection device according to claim 6, wherein one end of the push block has a protrusion which facilitates pushing the linkage mechanism.

8. The electric injection device according to claim 1, wherein a pulley is pivotally installed on the swing end.

9. The electric injection device according to claim 1, wherein the release blockage includes an oblique plane, a release elastic element and a button exposed to the outside of the outer case, in which the narrower part of the oblique plane is for the back stop element to abut and push against, the two ends of the release elastic element respectively abut against the inner side of the outer case and one end of the oblique plane, and the resetting block includes a resetting elastic element and extends to a sleeve block, in which the two ends of the resetting elastic element respectively abut against the resetting block and one side of the second stop block, the sleeve block goes through the second stop block and is sleeved on the pushing shaft between the second stop block and the pushing element, such that the oblique plane can squeeze and press the release elastic element after pressing down the button, thus making the back stop element push against the wider part of the oblique plane to position the back stop element in a vertical status, while the back stop element also squeezes and presses the resetting block, the resetting elastic element and the sleeve block located on the other side, allowing the sleeve block to squeeze and press the pushing element so as to position the pushing element in a vertical status; at this moment, the pushing shaft designed for preventing backward movement can be released for refilling the syringe, and after completing the refilling process, the release elastic element and the resetting elastic element are automatically reset by elastic force, so that the back stop element or the pushing element can present an inclined status once again.

10. The electric injection device according to claim 1, wherein the one or more abutting blocks comprise a plurality of abutting blocks and are configured to have a plurality of different lengths and collectively installed in a stroke control mechanism which is set up on the outer case and has a rotating block located inside of the outer case, and such abutting blocks are evenly installed on the outside of the rotating block which is provided with an inner axle, and the inner axle penetrates through the outer case and extends to configure a control disc at the exterior, and one side of the control disc is installed with a snap elastic element, and the outer surface of the second case is provided with a plurality of fixation holes around the center of the inner axle, and the snap elastic element can be stuck and fixed in one of the fixation holes at a predetermined angle.

11. The electric injection device according to claim 10, wherein the control disc shows a number of segments for controllable strokes.

12. The electric injection device according to claim 11, wherein the number of the plurality of abutting blocks, the number of segments and the number of fixation holes are equal.

13. The electric injection device according to claim 11, wherein the number of segments is four, and the lengths of the plurality of abutting blocks are respectively configured to 0.6 mm, 0.4 mm, 0.3 mm and 0.24 mm.

* * * * *